(12) United States Patent
Bonrath

(10) Patent No.: US 6,198,006 B1
(45) Date of Patent: Mar. 6, 2001

(54) PROCESS FOR THE MANUFACTURE OF CITRAL

(75) Inventor: Werner Bonrath, Freiburg (DE)

(73) Assignee: Roche Vitamins Inc., Parsippany, NJ (US)

(*) Notice: Subject to any disclaimer, the term of this patent is extended or adjusted under 35 U.S.C. 154(b) by 0 days.

(21) Appl. No.: 09/268,801

(22) Filed: Mar. 16, 1999

(30) Foreign Application Priority Data

Mar. 30, 1998 (EP) .................................................. 98105757

(51) Int. Cl.$^7$ .................................................. C07C 45/51
(52) U.S. Cl. .................... 568/485; 568/450; 568/449; 568/467; 568/488; 568/490; 568/492
(58) Field of Search .................... 568/386, 310, 568/341, 427, 450, 443, 449, 467, 485, 488, 490, 492

(56) References Cited

U.S. PATENT DOCUMENTS 4,749,814   6/1988   Chabardes ............................ 568/384

FOREIGN PATENT DOCUMENTS 0 240 431   7/1987   (EP) .
1 204 754   9/1970   (GB) .

OTHER PUBLICATIONS

Meyer, K.H., et al., *Ber. Deutsch Chem. Ges.* 55, 819–823 (1922).
Rupe, H., et al., *Helv. Chim. Acta.* 9, 672 (1926).
Saucy, G., et al., *Helv. Chim. Acta.* 42, 1945–1955 (1959).
Pauling, H., *Chimia.* 27, 383 (1973).
Pauling, H., et al., *Helv. Chim. Acta* 59, 1233–1243 (1976).
*Chem. Abs:* 114, 122769a (1991).
Erman, M.B., et al. *Mendeleev Commun.* 89 (1994).
Chabardes, P., *Tetr. Lett.* 29(48), 6253–6256 (1988).
Erman, M.B., et al., *Tetr. Lett.* 34, 2981–2984 (1976).
Lorber, C. Y., et al. *Tetr. Lett.* 37(6):853–856 (1996).
Kantam, M.L., et al. *Synth. Commun.* 23(1): 45–48 (1993).

*Primary Examiner*—Sreeni Padmanabhan
(74) *Attorney, Agent, or Firm*—Mark E. Waddell; Stephen M. Haracz; Bryan Cave LLP

(57) ABSTRACT

A process for the manufacture of citral is provided by the catalyzed rearrangement of dehydrolinalool to citral. The rearrangement is carried out in the presence of a molybdenum compound of the general formula $MoO_2X_2$ wherein X signifies an acetylacetonate or halide ion, and a dialkyl or diaryl sulphoxide as the catalyst system, in the presence of an organic acid having a pK value in the range of about 4.0 to about 6.5 and in an apolar aprotic organic solvent.

20 Claims, No Drawings

PROCESS FOR THE MANUFACTURE OF CITRAL

FIELD OF THE INVENTION

The present invention is concerned with a process for the manufacture of citral. The α,β-unsaturated aldehyde citral (E/Z-3,7-dimethyl-2,6-octadienal, consisting of the isomers geranial, i.e. E-citral, and neral, i.e. Z-citral) is, as is known, a valuable intermediate for the synthesis of odorants, terpinoids and vitamins.

BACKGROUND OF THE INVENTION

α,β-Unsaturated carbonyl compounds are generally important intermediates for the manufacture of odorants, vitamins and carotenoids [see, for example, Chem. Ztg. 97, 23–28 (1973) and Chap. VI ("Total Syntheses") in "Carotenoids", Ed. Otto Isler, published by Birkhäuser Basel and Stuttgart, 1971]. Their production by acid-catalyzed rearrangement of α-alkynols has already been described in the nineteen twenties by K. H. Meyer and K. Schuster [Ber. deutsch. Chem. Ges. 55, 819–823 (1922)] and H. Rupe and E. Kambli [Helv. Chim. Acta 9, 672 (1926)]; the isomerization of secondary or tertiary αalkynols to α,β-unsaturated carbonyl compounds has also generally become known as the Meyer-Schuster or Rupe-Kambli rearrangement. In the case of the rearrangement of a carbonyl compound having a terminal alkynyl group there are obtained aldehydes, otherwise ketones are the rearrangement products:

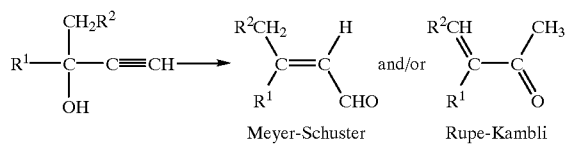

Meyer-Schuster     Rupe-Kambli wherein $R^1$ and $R^2$ each signify hydrogen or an aliphatic or aromatic residue. In addition to citral, the likewise α,β-unsaturated aldehydes citronellal and hydroxycitronellal are also of particular industrial interest, namely as intermediates for the manufacture of odorants, terpinoids and vitamins; citral itself can be converted, in each case in several process steps, into the important starting materials for the manufacture of d,l-α-tocopherol (vitamin E) and vitamin A, isophytol or β-ionone [see, for example, "Vitamine I, Fettlösliche Vitamine", Ed. Otto Isler and Georg Brubacher, published by Georg Thieme Stuttgart, New York 1982, the Chapter VI "Total Syntheses" in "Carotenoids" (published by Birkh äuser 1971) and the literature references referred to therein].

Depending on the reaction conditions, the rearrangement of dehydrolinalyl acetate catalyzed by silver or copper ions yields, according to G. Saucy et al. [Helv. Chim. Acta 42, 1945–1955 (1959)], a mixture of "allene acetate" (1-acetoxy-3,7-dimethyl-octa-1,2,6-triene) and "diacetate" (1,1-diacetoxy-3,7-dimethyl-octa-2,6-diene), which can hydrolyze to citral:

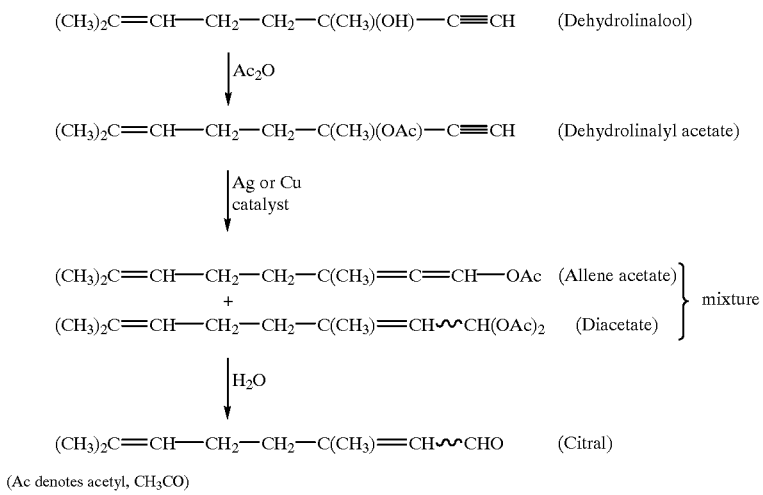

(Ac denotes acetyl, $CH_3CO$)

This rearrangement of dehydrolinalyl acetate is also known as the Saucy-Marbet rearrangement. However, dehydrolinalool can be converted directly into citral using an alkyl, cycloalkyl or aryl orthovanadate or another vanadium catalyst (UK Patent 1,204,754). Disadvantages in the direct conversion are, however, the low yield (about 31–37%) as well as the formation of dark precipitates which lead to the decomposition of the reaction solution. The direct rearrangement of dehydrolinalool is effected substantially more selectively and efficiently using tris(triphenylsilyl)vanadium oxide at about 140° C. [Chimia 27, 383 (1973) as well as Helv. Chim. Acta 59, 1233–1243 (1976)]. In this case yields of about 78% are achieved in paraffin oil as the solvent.

Further publications of the direct rearrangement of dehydrolinalool to citral using vanadium-containing catalysts include the use of polyboroxyvanadoxydiphenylsilane and of polysilylvanadates as the catalysts [Czechoslovakian Patent CS 264, 720/Chem. Abs. 114, 122769a (1991) and, respectively, Mendeleev Commun. 1994, 89]. Whereas in the first process the achieved yield of about 70% is too low commercially, an 80% yield can be achieved with the second process.

A further catalyst for the direct rearrangement of α-alkynyls, such as, for example, dehydrolinalool, to α,β-unsaturated carbonyl compounds consists of the combination of a titanium compound, e.g. titanium tetrachloride or tetrabutoxide, with a copper or silver halide [Tetr. Lett. 29, 6253–6256 (1988) and European Patent Publication 0 240 431 A]. However, the use of copper compounds is disadvantageous in this process. Moreover, also in this case, the about 64% yield of citral which is achieved is unsatisfactory.

An interesting variant of the aforementioned Meyer-Schuster rearrangement has been described briefly by C. Y. Lorber and J. A. Osborn in Tetr. Lett. 37, 853–856 (1996); this is the rearrangement of methylbutynol to prenal using a molybdenum catalyst. In this case, methylbutynol is rearranged to prenal in ortho-dichlorobenzene as the solvent in the presence of the catalyst system molybdenyl acetylacetonate, dibutyl sulphoxide and 4-tert.butylbenzoic acid. Although the yield in this rearrangement is indicated to be 97%, the prenal was not isolated from the reaction mixture, but the stated yield was obtained by gas-chromatographical analysis of the crude product. Presumably, it was difficult to work up the reaction mixture in order to isolate prenal.

L. A. Kheifits and co-workers found that dehydrolinalool could be converted into citral only in 28% yield and into 2-hydroxymethyl-1-methyl-3-isopropenylcyclopent-1-ene in 12% yield at 170° C. in a reaction period of 14 hours when a molybdenum catalyst produced from molybdenum oxide and triphenylsilanol was used for the rearrangement [Tetr. Lett. 34, 2981–2984 (1976)].

From the above remarks it is evident that the previously known processes for the catalyzed rearrangement of $\alpha$-alkynols, e.g. dehydrolinalool, to $\alpha,\beta$-unsaturated aldehydes, e.g. citral, have serious disadvantages.

SUMMARY OF THE INVENTION

The process in accordance with the invention is a process for the manufacture of citral by the catalyzed rearrangement of dehydrolinalool to citral, which process comprises carrying out the rearrangement in the presence of a molybdenum compound of the general formula:

$$MoO_2X_2 \qquad\qquad I$$

wherein X signifies an acetylacetonate or halide ion, and a dialkyl or diaryl sulphoxide as the catalyst system, in the presence of an organic acid having a pK value in the range of about 4.0 to about 6.5 and in an apolar aprotic organic solvent.

The components are added together and mixed. The reaction mixture is heated to the temperature at which the catalytic rearrangement reaction occurs, to provide a resulting mixture. Citral is then isolated from the resulting mixture.

DETAILED DESCRIPTION IF THE INVENTION

The process of the present invention surprisingly achieves a substantial yield of citral using a catalyst system which includes the known molybdenum compound molybdenyl acetylacetonate [also known as dioxomolybdenum (VI) acetylacetonate] or a molybdenyl halide.

The molybdenum compound of formula I, i.e., molybdenyl acetylacetonate (conventionally denoted as $MoO_2acac_2$) or a molybdenyl halide of the formula $MoO_2(Hal)_2$ [X=Hal], wherein Hal signifies chlorine or bromine, is in each case a readily obtainable known compound. The molybdenyl halide is preferably molybdenyl chloride, $MoO_2Cl_2$. However, the preferred molybdenum compound of formula I is molybdenyl acetylacetonate.

The dialkyl or diaryl sulphoxide likewise present in the catalyst system is especially a dialkyl sulphoxide, the alkyl groups of which are each straight-chain or branched and contain up to 8 carbon atoms, or a diaryl sulphoxide, the aryl groups of which in each case are optionally substituted phenyl groups. In the latter case, the substituents which may be present are especially $C_{1-4}$-alkyl groups, with the phenyl groups being in each case mono- or multiply-substituted by alkyl. Examples of both types of sulphoxides are dimethyl sulphoxide and dibutyl sulphoxide and, respectively, diphenyl sulphoxide and di(p-tolyl)sulphoxide. Dimethyl sulphoxide is preferably used as the sulphoxide.

As organic acids having a pK value in the range of about 4.0 to about 6.5 there come into consideration, inter alia, optionally halogenated, saturated and unsaturated aliphatic carboxylic acids, e.g. acetic acid (pK value 4.74), propionic acid (4.87), chloropropionic acid (3.98) and pivalic acid (5.01) or acrylic acid (4.25); alkanedicarboxylic acids, e.g. adipic acid (4.40); aryl-substituted alkanecarboxylic acids, e.g. phenylacetic acid (4.25); as well as aromatic carboxylic acids, e.g. benzoic acid (4.19) and 4-tert.butyl-benzoic acid (6.50). An organic acid having a pK value in the range of about 4.25 to about 6.5, especially phenylacetic acid having the pK value 4.25, is preferably used.

As solvents there can be used in the scope of the present invention in general apolar aprotic organic solvents, especially aliphatic, cyclic and aromatic hydrocarbons, such as, for example, $C_{7-10}$-alkanes, $C_{5-7}$-cycloalkanes, benzene, toluene and naphthalene as well as mixtures of such solvents with one another, e.g. paraffin oil (a mixture of saturated aliphatic hydrocarbons). Toluene is an especially preferred solvent.

The rearrangement is conveniently effected at temperatures in the range of about 80° C. to about 140° C., preferably at temperatures of about 90° C. to about 120° C.

The amount of molybdenum compound of formula I is conveniently about 0.1–8 mol % based on the amount of dehydrolinalool (educt) employed. This amount is preferably about 1–7 mol %, particularly about 3–5 mol %.

Furthermore, the weight ratio of dialkyl or diaryl sulphoxide to educt is conveniently about 0.2:1 to about 1:1; the weight ratio of acid to educt is conveniently about 0.02:1 to about 0.1:1, preferably about 0.04:1 to about 0.07:1, especially about 0.05:1; and the weight ratio of solvent to educt is conveniently about 5:1 to about 15:1, preferably about 7:1 to about 10:1.

The process in accordance with the invention can be carried out on an industrial scale very simply by adding the educt, the catalyst system (molybdenum compound of formula I as well as dialkyl or diaryl sulphoxide) and the organic acid to the solvent and heating the reaction mixture, which normally consists of a suspension because of the different solubilities of the reactants, to the reaction temperature. The rearrangement reaction is effected at temperatures of from about 80° C. to about 140° C., preferably at temperatures of from about 90° C. to about 120° C. Typically, the reaction mixture is heated to about 100° C. The sequence in which the addition is carried out is not critical, and therefore, for example, the acid or the sulphoxide can be added last.

In order to determine the course of the reaction, samples of the reaction mixture can be withdrawn and analysed according to known methods, e.g. thin-layer chromatography or gas chromatography. After completion of the reaction, the reaction period normally being up to about 20 hours, preferably up to about 7 hours, the working up can be effected by conventional procedures of organic chemistry. Typically, the mixture is filtered and the citral product is isolated from the filtrate by evaporation. For purification of the product, the crude material can, for example, be distilled.

The process in accordance with the invention is illustrated by the following Examples:

EXAMPLE 1
Rearrangement in Different Solvents 6.02 g (39.62 mmol) of dehydrolinalool (hereinafter "DLL"), 2.31 g (29.67 mmol) of dimethyl sulphoxide (hereinafter "DMSO"), 0.65 g (1.99 mmol) of molybdenyl acetyl-acetonate (hereinafter "MoO$_2$acac$_2$") and 2.60 g (14.58 mmol) of 4-tert.butylbenzoic acid in 50 ml of solvent were placed in a 100 ml sulphonation flask provided with a thermometer, stirrer and condenser. Subsequently, the mixture was heated to 100° C. During this the reaction mixture changed in colour from dark blue or dark green-blue depending on the process variant. For determining the course of the reaction, samples were removed and analysed by thin-layer chromatography (TLC) or gas chromatography (GC). After completion of the reaction the mixture was worked up by filtration over a small amount of silica gel and subsequent concentration under reduced pressure. The content determination was effected by GC using an internal standard. The results compiled in Table 1 hereinafter were obtained:

TABLE 1

| Solvent | Yield of citral | Residual DLL |
|---|---|---|
| Toluene | 88% | 0% |
| Paraffin oil | 80% | 10% |

EXAMPLE 2
Rearrangement in the Presence of Different Acids 6.02 g (39.62 mmol) of DLL, 2.31 g (29.67 mmol) of DMSO and 0.65 g (1.99 mmol) of MoO$_2$acac$_2$ in 50 ml of toluene were placed in a 100 ml sulphonation flask provided with a thermometer, stirrer and condenser and treated with in each case 14.58 mmol of acid. Subsequently, the mixture was heated to 100° C. and, after completion of the reaction (TLC and GC control), worked up as described in Example 1. The results compiled in Table 2 hereinafter were obtained:

TABLE 2

| | Yield of: | | | |
|---|---|---|---|---|
| Acid | Neral (Z-citral) | Geranial (E-citral) | Citral (total) | Residual DLL |
| Stearic acid | 30.84% | 36.98% | 67.82% | 14.12% |
| Acetic acid | 23.16% | 27.74% | 50.90% | 26.30% |
| Benzoic acid | 29.59% | 47.48% | 77.07% | 0% |
| Propionic acid | 28.99% | 33.97% | 62,97% | 28.02% |
| Pivalic acid | 36.26% | 44.55% | 80.81% | 0% |
| Acrylic acid | 37.00% | 46.66% | 83.65% | 0% |
| Adipic acid | 39.07% | 45.23% | 84.30% | 0% |
| Phenylacetic acid | 38.92% | 47.85% | 86.77% | 6.83% |
| 4-tert.Butylbenzoic acid | 39.35% | 48.27% | 87.63% | 1.10% |

EXAMPLE 3
Determination of a Typical Reaction Course 6.02 g (39.62 mmol) of DLL, 2.32 g (29.67 mmol) of DMSO, 0.65 g (1.983 mmol) of MoO$_2$acac$_2$ and 1.99 g (14.98 mmol) of phenylacetic acid in 50 ml of toluene were heated to 100° C. in a 100 ml sulphonation flask provided with a thermometer, stirrer and condenser. The mixture was stirred at this temperature for 23.5 hours and samples were withdrawn at specific time intervals and analysed by GC or TLC. For the gas chromatography, 700 µl of reaction solution were withdrawn and freed from catalyst by rapid filtration. This sample was weighed and analysed by GC. The yields compiled in Table 3 hereinafter were obtained:

TABLE 3

| | Content of: | | | | | | |
|---|---|---|---|---|---|---|---|
| Time (hours) | DLL | Neral | | Geranial | | Citral | |
| 0 | 100.00% | 0 | + | 0 | → | 0 | |
| 1 | 77.68% | 12.96 | + | 8.75 | → | 21.71% | |
| 2 | 57.60% | 23.84 | + | 17.87 | → | 41.71% | |
| 3 | 46.71% | 29.49 | + | 23.18 | → | 52.67% | |
| 4 | 29.59% | 37.82 | + | 32.60 | → | 70.42% | |
| 5 | 18.15% | 42.21 | + | 39.00 | → | 81.21% | |
| 6 | 11.54% | 44.27 | + | 43.55 | → | 87.82% | |
| 7 | 7.14% | 45.25 | + | 46.94 | → | 92.19% | |
| 8 | 4.20% | 44.99 | + | 50.23 | → | 95.22% | |
| 23.5 | 0% | 37.38 | + | 60.70 | → | 98.08% | |

EXAMPLE 4

6.02 g (39.62 mmol) of DLL, 2.31 g (29.67 mmol) of DMSO, 1.99 g (14.88 mmol) of phenylacetic acid and 0.65 g (1.983 mmol) of MoO$_2$acac$_2$ in 50 ml of toluene were heated to 100° C. in a 100 ml sulphonation flask provided with a stirrer, thermometer and condenser. After a reaction period of 17 hours the mixture was cooled to room temperature, filtered over 10 g of silica gel and rinsed with 100 ml of toluene. The filtrate was concentrated to constant weight at 25 mbar (2.5 KPa) and 40° C. 11.89 g of a yellow-brown crude product were obtained. The content determination was effected by GC. The results found were:

| Content: | Neral 21.08% | Geranial 22.55% |
|---|---|---|
| Yield: | Neral 2.51 g (41.63%) | Geranial 2.68 g (44.54%) |

This gives a yield of citral (E+Z) of 5.19 g (86.17%). Furthermore, 2.08% (0.25 g) of unreacted DLL were found. Accordingly, 89.95% of the reacted 5.77 g of DLIL were rearranged into citral.

EXAMPLE 5

6.02 g (39.62 mmol) of DLL, 2.31 g (29.67 mmol) of DMSO, 2.60 g (14.58 mmol) of 4-tert.butylbenzoic acid and 0.65 g (1.983 mmol) of MoO$_2$acac$_2$ in 50 ml of toluene were heated to 100° C. in a 100 ml sulphonation flask provided with a stirrer, thermometer and condenser. After a reaction period of 17 hours the mixture was cooled to room temperature, filtered over 10 g of silica gel and rinsed with 100 ml of toluene. The filtrate was concentrated to constant weight at 25 mbar (2.5 KPa) and 40° C. 11.05 g of a yellow-brown crude product were obtained. The content determination was effected by GC. The results found were:

| Content: | Neral 21.44% | Geranial 26.30% |
|---|---|---|
| Yield: | Neral 2.37 g (39.35%) | Geranial 2.91 g (48.27%) |

This gives a yield of citral (E+Z) of 5.27 g (87.63%). Furthermore, 1.10% (0.12 g) of unreacted DLL were found. Accordingly, 89.32% of the reacted 5.90 g of DLL were rearranged into citral.

EXAMPLE 6

6.02g (39.62 mmol) of DLL, 2.31 g (29.67 mmol) of DMSO, 1.78 g (14.58 mmol) of benzoic acid and 0.65 g (1.983 mmol) of $MoO_2acac_2$ in 50 ml of toluene were heated to 100° C. in a 100 ml sulphonation flask provided with a stirrer, thermometer and condenser. After a reaction period of 17 hours the mixture was cooled to room temperature, filtered over 10 g of silica gel and rinsed with 100 ml of toluene. The filtrate was concentrated to constant weight at 25 mbar (2.5 KPa) and 40° C. 9.35 g of a yellow-brown crude product were obtained. The content determination was effected by GC. The following results were found:

| Content: | Neral 19.05% | Geranial 30.09% |
| --- | --- | --- |
| Yield: | Neral 1.78 g (29.59%) | Geranial 2.86 g (47.48%). |

This gives a yield of citral (E+Z) of 4.63 g (77.07%). No DLL was found.

EXAMPLE 7

6.02 g (39.62 mmol) of DLL, 2.31 g (29.67 mmol) of DMSO, 2.13 g (14.58 mmol) of adipic acid and 0.65 g (1.983 mmol) of $MoO_2acac_2$ in 50 ml of toluene were heated to 100° C. in a 100 ml sulphonation flask provided with a stirrer, thermometer and condenser. After a reaction period of 17 hours the mixture was cooled to room temperature, filtered over 10 g of silica gel and rinsed with 100 ml of toluene. The filtrate was concentrated to constant weight at 25 mbar (2.5 KPa) and 40° C. 6.41 g of a yellow-brown crude product were obtained. The content determination was effected by GC. The following results were found:

| Content: | Neral 36.69% | Geranial 42.48% |
| --- | --- | --- |
| Yield: | Neral 2.35 g (39.07%) | Geranial 2.72 g (45.23%) |

This gives a yield of citral (E+Z) of 5.07 g (84.30%). No DLL was found.

From the foregoing description, one skilled in the art can ascertain the essential characteristics of this invention, and without departing from the spirit and scope thereof, can make various changes and modifications. Preferred embodiments set forth by way of illustration are not intended as limitations on the variations possible in practising the present invention.

What is claimed is:

1. A process for the manufacture of citral by the catalytic rearrangement of dehydrolinalool to citral, which process comprises
    (a) carrying out the rearrangement of dehydrolinalool in the presence of a molybdenum compound of the general formula $MoO_2X_2$ wherein X is an acetylacetonate or halide ion, a dialkyl or diaryl sulphoxide, and an organic acid having a pK value of from about 4.0 to about 6.5, in an apolar aprotic organic solvent; and
    (b) isolating the citral from the resulting mixture.
2. The process according to claim 1, wherein the molybdenum compound is molybdenyl acetylacetonate or molybdenyl chloride.
3. The process according to claim 2, wherein the molybdenum compound is molybdenyl acetylacetonate.
4. The process according to claim 1, wherein the dialkyl or diaryl sulphoxide is taken from the group consisting of dimethyl sulphoxide, dibutyl sulphoxide, diphenyl sulphoxide and di(p-tolyl) sulphoxide.
5. The process according to claim 4, wherein the dialkyl sulphoxide is dimethyl sulphoxide.
6. The process according to claim 1, wherein the organic acid is taken from the group consisting of saturated aliphatic carboxylic acids, unsaturated aliphatic carboxylic acids, halogenated saturated aliphatic carboxylic acids, halogenated unsaturated aliphatic carboxylic acids, alkanedicarboxylic acids, aryl-substituted alkanecarboxylic acids and aromatic carboxylic acids.
7. The process according to claim 6, wherein the organic acid is taken from the group consisting of acetic acid, propionic acid, chloropropionic acid, pivalic acid, acrylic acid, adipic acid, phenylacetic acid, benzoic acid and 4-tert.butyl-benzoic acid.
8. The process according to claim 7, wherein the organic acid is phenylacetic acid.
9. The process according to claim 1, wherein the solvent is taken from the group consisting of aliphatic hydrocarbons, cyclic hydrocarbons, aromatic hydrocarbons and mixtures thereof.
10. The process according to claim 9, wherein the solvent is taken from the group consisting of a $C_{7-10}$-alkane, a $C_{5-7}$-cycloalkane, benzene, toluene, naphthalene and paraffin oil.
11. The process according to claim 10, wherein the solvent is toluene.
12. The process according to claim 1, wherein the rearrangement is effected at a temperature of from about 80° C. to about 140° C.
13. The process according to claim 12, wherein the rearrangement is effected at a temperature of from about 90° C. to about 120° C.
14. The process according to claim 1, wherein the amount of molybdenum compound is from about 0.1 to about 8 mol % based on the amount of dehydrolinalool employed.
15. The process according to claim 14, wherein the amount of molybdenum compound is from about 1 to about 7 mol %.
16. The process according to claim 1, wherein the weight ratio of dialkyl or diaryl sulphoxide to dehydrolinalool (DLL) is from about 0.2:1 to about 1:1; the weight ratio of acid to DLL is from about 0.02:1 to about 0.1:1 and the weight ratio of solvent to DLL is from about 5:1 to about 15:1.
17. The process according to claim 16, wherein the weight ratio of acid to DLL is from about 0.04:1 to about 0.07:1.
18. The process according to claim 17, wherein the weight ratio of acid to DLL is about 0.05:1.
19. The process according to claim 16, wherein the weight ratio of solvent to DLL is from about 7:1 to about 10:1.
20. A process for the manufacture of citral by the catalytic rearrangement of dehydrolinalool to citral, comprising:
    (a) mixing dehydrolinalool, a molybdenum compound of the general formula $MoO_2X_2$ wherein X is an acetylacetonate or halide ion, a dialkyl or diaryl sulphoxide, and organic acid having a pK value of from about 4.0 to about 6.5 and an apolar aprotic organic solvent to provide a reaction mixture;
    (b) heating the reaction mixture to the temperature at which the catalytic rearrangement reaction occurs to provide a resulting mixture; and
    (c) isolating the citral from the resulting mixture.

* * * * *